United States Patent [19]

Raddatz et al.

[11] Patent Number: 4,721,776
[45] Date of Patent: Jan. 26, 1988

[54] AMINO ACID DERIVATIVES

[75] Inventors: Peter Raddatz, Darmstadt; Günter Hölzemann, Seeheim; Claus J. Schmitges, Umstadt; Klaus O. Minck, Ober-Ramstadt, all of Fed. Rep. of Germany

[73] Assignee: Merck Patent Gesellschaft Mit Beschrankter Haftung, Darmstadt, Fed. Rep. of Germany

[21] Appl. No.: 930,483

[22] Filed: Nov. 14, 1986

[30] Foreign Application Priority Data

Nov. 15, 1985 [DE] Fed. Rep. of Germany ....... 3540495

[51] Int. Cl.$^4$ .................... A61K 37/64; C07C 103/52; C12Q 1/36
[52] U.S. Cl. .................................. 530/323; 530/329; 530/330; 530/331; 530/332; 514/17; 514/18; 514/19
[58] Field of Search ............... 530/323, 329, 330, 331, 530/332; 514/17, 18, 19

[56] References Cited

U.S. PATENT DOCUMENTS

| | | | |
|---|---|---|---|
| 4,424,207 | 1/1984 | Szelke et al. ................ | 530/327 |
| 4,609,643 | 9/1986 | Szelke et al. ................ | 530/328 |
| 4,638,047 | 1/1987 | Szelke et al. ................ | 530/328 |
| 4,645,759 | 2/1987 | Luly et al. ................... | 530/331 |
| 4,650,661 | 3/1987 | Szelke et al. ................ | 530/323 |
| 4,652,551 | 3/1987 | Luly et al. ................... | 514/18 |
| 4,657,931 | 4/1987 | Baran et al. ................. | 530/331 |
| 4,663,310 | 5/1987 | Bock et al. .................. | 530/330 |
| 4,665,055 | 5/1987 | Evans ......................... | 514/18 |
| 4,666,888 | 5/1987 | Raddatz et al. ............. | 514/18 |
| 4,668,770 | 5/1987 | Boger et al. ................. | 530/331 |

FOREIGN PATENT DOCUMENTS

| | | |
|---|---|---|
| 077028 | 4/1983 | European Pat. Off. . |
| 0155809 | 9/1985 | European Pat. Off. ............ 5/6 |
| 0156321 | 10/1985 | European Pat. Off. . |
| 84/03044 | 8/1984 | PCT Int'l Appl. . |

OTHER PUBLICATIONS

Chem Abstracts, vol. 97 (1982) 39405p.

*Primary Examiner*—Delbert R. Phillips
*Assistant Examiner*—Nathan M. Nutter
*Attorney, Agent, or Firm*—Millen & White

[57] ABSTRACT

New amino acid derivatives of the formula I $$X-Z-NR^2-CHR^3-CHR^4-(CHR^5)_nCO-B-D \qquad I$$

in which X, Z, $R^2$, $R^3$, $R^4$, $R^5$, B, D and n have the meanings defined herein, and their salts inhibit the activity of human plasma renin.

17 Claims, No Drawings

AMINO ACID DERIVATIVES

BACKGROUND OF THE INVENTION

The invention relates to new amino acid derivatives.

SUMMARY OF THE INVENTION

It is an object of this invention to provide new compounds with valuable properties, in particular those which can be used for the preparation of medicaments.

Upon further study of the specification and appended claims, further objects and advantages of this invention will become apparent to those skilled in the art.

These objects have been achieved by providing new amino acid derivatives of the formula I

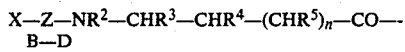

in which

X is H, $R^1$—O—$C_mH_{2m}$—CO—, $R^1$—$C_mH_{2m}$—O—CO—, $R^1$—$C_mH_{2m}$—CO—, $R^1$—$SO_2$—, ($R^1$—$C_mH_{2m}$)—L($R^1$—$C_pH_{2p}$)—$C_rH_{2r}$—CO—, H—(NHCH$_2$CH$_2$)$_m$—NH—CH$_2$CO— or 9-fluorenyl—$C_mH_{2m}$—O—CO—, Z is 0 to 4 amino acid residues which are bonded together in the manner of a peptide and selected from the group comprising Abu, Ada, Ala, Arg, Asn, Bia, Cal, Dab, Gln, Gly, His, N(im)-alkyl-His, Ile, Leu, tert.-Leu, Lys, Met, αNal, βNal, Nbg, Nle, Orn, Phe, Pro, Ser, Thr, Tic, Trp, Tyr and Val, B is absent or is Abu, Ala, Cal, Gly, Ile, Leu, Met, Nle or Val, D is

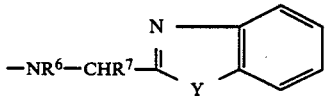

(in which it is also possible for one or more CH groups in the benzene ring to be replaced by N), Y is NH, O or S, $R^1$ and $R^3$ are each A, Ar, Ar-alkyl, or, in each case unsubstituted or substituted once or several times by A, AO and/or Hal, cycloalkyl which has 3–7 C atoms, cycloalkyl-alkyl which has 4–11 C atoms, bicycloalkyl or tricycloalkyl, each of which have 7–14 C atoms, or bicycloalkylalkyl or tricycloalkylalkyl, each of which have 8–18 C atoms, $R^2$, $R^5$ and $R^6$ are each H or A, $R^4$ is OH or $NH_2$, $R^7$ is H, A, cycloalkylalkyl or Ar-alkyl, L is CH or N, m, p and r are each 0, 1, 2, 3, 4 or 5, n is 1 or 2, Ar is phenyl which is unsubstituted or substituted once or several times by A, AO, Hal, $CF_3$, OH and/or $NH_2$, or is unsubstituted naphthyl, Hal is F, Cl, Br or I, and A is alkyl which has 1–8 C atoms, in which, furthermore, it is also possible for one or more —NH—CO— groups to be replaced by one or more —NA—CO— groups, and their salts.

In the foregoing, selection of variables defined together is made independently.

Similar compounds are disclosed in European Pat. No. A-77028.

It has been found that the compounds of the formula I and their salts have very valuable properties. In particular, they inhibit the activity of human plasma renin. This action can be demonstrated by, for example, the method of F. Fyhrquist et al., Clin. Chem. 22, 250–256 (1976). It is noteworthy that these compounds are very specific inhibitors of renin; as a rule, to inhibit other aspartyl proteinases (for example pepsin and cathepsin D) considerably higher concentrations of these compounds are necessary, e.g., 100 to 10,000 times as high.

The compounds can be used as active compounds for medicaments in human and veterinary medicine, in particular for the prophylaxis and for the treatment of disorders of the heart, circulation and vessels, especially of hypertension, cardiac insufficiency and hyperaldosteronism. In addition, the compounds can be used for diagnostic purposes in order to determine in patients with hypertension or hyperaldosteronism the possible contribution of renin activity to maintenance of the pathological condition. Such diagnostic tests can be performed in the manner disclosed in EP-A-77028.

The abbreviations of amino acid residues mentioned heretofore and hereinafter represent the residues —NH—CHR—CO— (in which R has the specific meaning known for each amino acid) of the following amino acids:

Abu 2-aminobutyric acid
Ada adamantylalanine
Ala alanine
Arg arginine
Asn asparagine
Bia benzimidazolylalanine
Cal cyclohexylalanine
Dab 2,4-diaminobutyric acid
Gln glutamine
Gly glycine
His histidine
N(im)-alkyl-His histidine substituted in the 1- or 3-position of the imidazole ring by A
Ile isoleucine
Leu leucine
tert.-Leu tert.-leucine
Lys lysine
Met methioine
αNal α-naphthylalanine
βNal β-naphthylalanine
Nbg (2-norbornyl)-glycine
Nle norleucine
N-Me-His N-methyl-histidine
N-Me-Phe N-methyl-phenylalanine
Orn ornithine
Phe phenylalanine
Pro proline
Ser serine
Thr threonine
Tic tetrahydroisoquinoline-1-carboxylic acid
Trp tryptophan
Tyr tyrosine
Val valine.

The following additional meanings are given:
BOC tert.butoxycarbonyl
imi-BOM benzyloxymethyl in the 1-position of the imidazole ring
CBZ benzyloxycarbonyl
DNP 2,4-dinitrophenyl
imi-DNP 2,4-dinitrophenyl in the 1-position of the imidazole ring
FMOC 9-fluorenylmethoxycarbonyl OMe methyl ester
OEt ethyl ester
POA phenoxyacetyl
DCCI dicyclohexylcarbodiimide
HOBt 1-hydroxybenzotriazole.

Where the abovementioned amino acids can occur in several enantiomeric forms, then all these forms as well as their mixtures (for example the DL-forms) are included, for example as constituent of the compounds of the formula I, heretofore and hereinafter. The L-forms are preferred. Where individual compounds are mentioned hereinafter, then the abbreviations of these amino acids relate in each case to the L-form, unless expressly indicated otherwise.

Heretofore and hereinafter the residues or parameters X, Z, B, D, Y, $R^1$ to $R^7$, L, m, n, p, r, Ar, Hal, A, $G^1$, $G^2$, $Z^1$, $Z^2$ and W have the meanings indicated for formulae I, II or III, unless expressly indicated otherwise.

In the formulae heretofore A has 1-8, preferably 1, 2, 3 or 4, C atoms. A is preferably methyl, but also ethyl, propyl, isopropyl, butyl, isobutyl, sec.-butyl or tert.-butyl, as well as pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, or 1,1,2- or 1,2,2-trimethylpropyl.

Cycloalkyl is preferably cyclopropyl, cyclobutyl, cyclopentyl, cyclohexyl or cycloheptyl, but also, for example, 1-, 2- or 3-methylcyclopentyl, or 1-, 2-, 3- or 4-methylcyclohexyl.

Correspondingly, cycloalkyl-alkyl is preferably cyclopropylmethyl, 2-cyclopropylethyl, cyclobutylmethyl, 2-cyclobutylethyl, cyclopentylmethyl, 2-cyclopentylethyl, cyclohexylmethyl, 2-cyclohexylethyl as well as, for example, 1-, 2- or 3-methylcylopentylmethyl, or 1-, 2-, 3- or 4-methylcyclohexylmethyl.

Bicycloalkyl is preferably 1- or 2-decalyl, 2-bicyclo[2.2.1]heptyl or 6,6-dimethyl-2-bicyclo[3.1.1]heptyl.

Tricycloalkyl is preferably 2-adamantyl.

Ar is preferably phenyl, and is also preferably o-, m- or p-tolyl, o-, m- or p-ethylphenyl, o-, m-, or p-methoxyphenyl, o-, m- or p-fluorophenyl, o-, m- or p-chlorophenyl, o-, m- or p-bromophenyl, o-, m- or p-iodophenyl, o-, m- or p-trifluoromethylphenyl, 2,3-, 2,4-, 2,5-, 2,6-, 3,4- or 3,5-dimethoxyphenyl, 3,4,5-trimethoxyphenyl, o-, m- or p-aminophenyl, or 1- or 2-naphthyl.

$R^1$ is preferably A, in particular methyl, ethyl, propyl, isopropyl, butyl, isobutyl or tert.-butyl, as well as preferably cyclopropyl, cyclopentyl, cyclohexyl, phenyl or benzyl.

$R^2$, $R^5$ and $R^6$ are preferably H or methyl, as well as ethyl, propyl, isopropyl, butyl or isobutyl.

$R^3$ is preferably cyclohexylmethyl, as well as preferably A, in particular methyl, ethyl, propyl, isopropyl, butyl, isobutyl, sec-butyl, pentyl, isopentyl (3-methylbutyl) or 2-methylbutyl, phenyl, benzyl, p-chlorobenzyl, 2-cyclohexylethyl, bicyclo[2.2.1]hept-2-ylmethyl or 6,6-dimethylbicyclo[3.1.1]hept-2-ylmethyl.

$R^4$ is preferably OH.

$R^7$ is preferably H, methyl, ethyl, isobutyl or sec.-butyl, as well as preferably propyl, butyl, cyclohexylmethyl or benzyl.

L is preferably CH.

Y is preferably NH.

m, p and r are preferably 0, 1 or 2; n is preferably 1.

X is preferably H, POA, alkoxycarbonyl such as BOC, CBZ, alkanoyl such as acetyl, propionyl, butyryl or isobutyryl, cycloalkylcarbonyl such as cyclopentylcarbonyl or cyclohexylcarbonyl, aroyl such as benzoyl, arylalkanoyl such as phenylacetyl, 2- or 3-phenylpropionyl, 4-phenylbutyryl, 2-benzyl-3-phenylpropionyl, 2-benzyl-4-phenylbutyryl, 2-(2-phenylethyl)-4-phenylbutyryl, 2-(2-naphthylmethyl)-4-phenylbutyryl, 2- or 3-o-, -m- or -p-fluorophenylpropionyl, 2- or 3-o-, -m-, or -p-chlorophenylpropionyl, cycloalkylalkanoyl such as cyclohexylacetyl, 2- or 3-cyclohexylpropionyl. Particularly preferred radicals X are H and BOC, as well as POA, 4-phenylbutyryl, 2-benzyl-3-phenylpropionyl, 2-benzyl-4-phenylbutyryl, 2-(2-phenylethyl)-4-phenylbutyryl, 2-(2-naphthylmethyl)-4-phenylbutyryl and CBZ.

Z is preferably 2, but also 0 or 1, as well as 3 or 4, amino acid residues which are bonded together in the manner of a peptide, in particular one of the groups His, Phe-His, Pro-Phe-His or His-Pro-Phe-His, as well as preferably the groups Abu, Aba, Asn, Bia, Cal, Gln, N-(im)-methyl-His, Leu, αNal, βNal, Nle, Phe, Trp, Tyr, Abu-His, Ada-His, Ala-His, Ala-Phe, Arg-His, Asn-His, Bia-His, Cal-His, Dab-His, Gly-His, His-His, UIe-His, Leu-His, tert.-Leu-His, Lys-His, Met-His, αNal-His, βNal-His, Nbg-His, Nle-His, (N-Me-His)-His, (N-Me-Phe)-His, Orn-His, Phe-Abu, Phe-Ada, Phe-Ala, Phe-Arg, Phe-Asn, Phe-Bia, Phe-Cal, Phe-Dab, Phe-Gln, Phe-Gly, Phe-(N-im-methyl-His), Phe-Ile, Phe-Leu, Phe-tert.-Leu, Phe-Lys, Phe-Met, Phe-α-Nal, Phe-β-Nal, Phe-Nbg, Phe-Nle, Phe-(N-Me-His), Phe-(N-Me-Phe), Phe-Orn, Phe-Phe, Phe-Pro, Phe-Ser, Phe-Thr, Phe-Tic, Phe-Trp, Phe-Tyr, Phe-Val, Pro-His, Ser-His, Thr-His, Tic-His, Trp-His, Tyr-His, Val-His, as well as Ada-Phe-His, Pro-Ala-His, Pro-Ala-Phe, Pro-Phe-Ala, Pro-Phe-Phe, HisPro-Ala-His, His-Pro-Ala-Phe, His-Pro-Phe-Phe, as well as Pro-Abu-His, Pro-Ada-His, Pro-Arg-His, Pro-Asn-His, Pro-Bia-His, Pro-Dab-His, Pro-Gly-His, Pro-His-His, Pro-Ile-His, Pro-Leu-His, Pro-tert.-Leu-His, Pro-Lys-His, Pro-Met-His, Pro-Nbg-His, Pro-Nle-His, Pro-(N-Me-His)-His, Pro-(N-Me-Phe)-His, Pro-Orn-His, Pro-Phe-Abu, Pro-Phe-Ada, Pro-Phe-Arg, Pro-Phe-Asn, Pro-Phe-Bia, Pro-Phe-Dab, Pro-Phe-Gln, Pro-Phe-Gly, Pro-Phe-(N-im-methyl-His), Pro-Phe-Ile, Pro-Phe-Leu, Pro-Phe-tert.-Leu, Pro-Phe-Lys, Pro-Phe-Met, Pro-Phe-Nbg, Pro-Phe-Nle, Pro-Phe-(N-Me-His), Pro-Phe-(N-Me-Phe), Pro-Phe-Orn, Pro-Phe-Pro, Pro-Phe-Ser, Pro-Phe-Thr, Pro-Phe-Tic, Pro-Phe-Trp, Pro-Phe-Tyr, PrO-Phe-Val, Pro-Pro-His, Pro-Ser-His, Pro-Thr-His, Pro-Tic-His, Pro-Trp-His, Pro-Tyr-His, Pro-Val-His, His-Pro-Abu-His, His-Pro-Ada-His, His-Pro-Arg-His, His-Pro-Asn-His, His-Pro-Bia-His, His-Pro-Dab-His, His-Pro-Gly-His, His-Pro-His-His, His-Pro-Ile-His, His-Pro-Leu-His, His-Pro-tert.-Leu-His, His-Pro-Lys-His, His-Pro-Met-His, His-Pro-Nbg-His, His-Pro-Nle-His, His-Pro-(N-Me-His)-His, His-Pro-(N-Me-Phe)-His, His-Pro-Orn-His, His-Pro-Phe-Abu, His-Pro-Phe-Ada, His-Pro-Phe-Arg, His-Pro-Phe-Asn, His-Pro-Phe-Bia, Bis-Pro-Phe-Dab, His-Pro-Phe-Gln, His-Pro-Phe-Gly, His-Pro-Phe(N-im-imethyl-His), His-Pro-Phe-Ile, His-Pro-Phe-Leu, His-Pro-Phe-tert.-Leu, His-Pro-Phe-Lys, His-Pro-Phe-Met, His-Pro-Phe-Nbg, His-Pro-Phe-Nle, His-Pro-Phe-(N-Me-His), His-Pro-Phe-(N-Me-Phe), His-Pro-Phe-Orn, His-Pro-Phe-Pro, His-Pro-Phe-Ser, His-Pro-Phe-Thr, His-Pro-Phe-Tic, His-Pro-Phe-Trp, His-Pro-Phe-Tyr, His-Pro-Phe-Val, His-Pro-Pro-His, His-Pro-Ser-His, His-Pro-Thr-His, His-Pro-Tic- His, His-Pro-Trp-His, His-Pro-Tyr-His, His-Pro-Val-His.

B is preferably absent or is preferably Ile or Leu, as well as preferably Abu, Cal, Met or Nle.

The heterocyclic ring in the radical D is preferably benzimidazol-2-yl, as well as preferably imidazo[4,5-b]pyridin-2-yl (=1,3,4-triazainden-2-yl), imidazo[4,5-c]pyridin-2-yl (=1,3,5-triazainden-2-yl) or imidazo[4,5-d]pyrimidin-2-yl (=purin-8-yl), as well as, for example, benzoxazol-2-yl, benzothiazol-2-yl, imidazo[4,5-b]pyrazin-2-yl (=1,3,4,7-tetraazainden-2-yl) or imidazo[4,5-d]pyridazin-2-yl (=1,3,5,6-tetraazainden-2-yl). If CH groups in the benzene ring in the radical D have been replaced by N, then preferably only one or two of these groups have been replaced by N.

The group W is preferably —NH—CHR$^3$—CHOH—CH$_2$—CO—, in particular —NH—CH(cyclohexylmethyl)—CHOH—CH$_2$—CO-("AHCP", derived from 4-amino-3-hydroxy-5-cyclohexylpentanoic acid), as well as —NH—CH(CH$_2$CH$_2$-cyclohexyl)-CHOH—CH$_2$—CO— ("AHCH"; derived from 4-amino-3-hydroxy-6-cyclohexylhexanoic acid), —NH—CH(isobutyl)—CHOH—CH$_2$—CO— ("Sta"; derived from statin) or —NH—CH(benzyl)—CHOH—CH$_2$—CO— ("AHPP"; derived from 4-amino-3-hydroxy-5-phenylpentanoic acid). The group W is also preferably —NH—CHR$^3$—CH(NH$_2$)—CH$_2$—CO—, in particular —NH—CH(cyclohexylmethyl)—CH(NH$_2$)—CH$_2$—CO— ("DACP"; derived from 3,4-diamino-5-cyclohexylpentanoic acid), —NH—CH(CH$_2$CH$_2$—cyclohexyl)—CH(NH$_2$)—CH$_2$—CO— ("DACH"; derived from 3,4-diamino-6-cyclohexylhexanoic acid), —NH—CH(isobutyl)—CH(NH$_2$)—CH$_2$—CO— ("DAMH"; derived from 3,4-diamino-6-methylheptanoic acid) or —NH—CH(benzyl)—CH(NH$_2$)—CH$_2$—CO— ("DAPP"; derived from 3,4-diamino-5-phenylpentanoic acid).

The group W has at least two chiral centres. The compounds of the formula I can thus occur in different forms which are optically inactive or optically active. Formula I embraces all these forms. If W is —NH—CHR$^3$—CHR$^4$—CH$_2$—CO—, then the 3S-hydroxy-4S-amino enantiomers or 3S,4S-diamino enantiomers are preferred. Unless otherwise specified in the name of individual substances, the abbreviations AHCP, AHCH, Sta, AHPP, DACP, DACH, DAMH and DAPP always relate to these 3S,4S-forms.

Accordingly, the invention particularly relates to those compounds of the formula I in which at least one of the said radicals has one of the preferred meanings indicated above. Some preferred groups of compounds can be expressed by the following part-formulae Ia to Ic which correspond to the formula I but in which
in Ia
X is H, BOC, POA, CBZ, 2-phenylbutyryl, 2-benzyl-3-phenylpropionyl, 2-benzyl-4-phenylbutyrl, 2-(2-phenylethyl-4-phenylbutyrl) or 2-(2-naphthylmethyl)-4-phenylbutyryl,
Z is absent or is His, Ada-His, Cal-His, αNal-His, βNal-His, Phe-Abu, Phe-Bia, Phe-DAB, Phe-His, Phe-N-(im)-methyl-His, Phe-Leu, Phe-Lys, Phe-Met, Phe-Nle or Phe-Orn,
R$^2$ and R$^5$ are H,
R$^3$ is isobutyl, cyclohexylmethyl, 2-cyclohexylethyl or benzyl,
n is 1,
B is absent or is Ile or Leu,
D is —NH—CHR$^7$-(benzimidazol-2-yl) and
R$^7$ is H or alkyl which has 1–4 C atoms;
In Ib
X is H, BOC, 2-benzyl-3-phenylpropionyl, 2-benzyl-4-phenylbutyryl or 2-(2-phenylethyl)-4-phenylbutyryl,
Z is His, Ada-His, Cal-His, α-Nal-His, β-Nal-His, Phe-Abu, Phe-Bia, Phe-Dab, Phe-His, Phe-N(im)-methyl-His, Phe-Leu, Phe-Lys, Phe-Met, Phe-Nle or Phe-Orn,
R$^2$ and R$^5$ are H,
R$^3$ is cyclohexylmethyl,
R$^4$ is OH,
n is 1,
B is absent or Ile,
D is —NH—CHR$^7$—(benzimidazol-2-yl) and
R$^7$ is H or alkyl which has 1–4 C atoms;
in Ic
X is BOC or 2-benzyl-4-phenylbutyryl,
Z is His or Phe-His,
R$^2$ and R$^5$ are each H,
R$^3$ is cyclohexylmethyl,
R$^4$ is OH,
n is 1,
B is absent or Ile,
D is —NH—CHR$^7$—(benzimidazol(2-yl) and
R$^7$ is H or isobutyl.

The preferred number of substituents in the substituted R$^1$, R$^3$ or Ar groups is 1–3, most preferably 1 or 2.

The invention also relates to a process for the preparation of an amino acid derivative of the formula I and of its salts, which is characterized in that it is liberated from one of its functional derivatives by treatment with a solvolyzing or hydrogenolyzing agent, or in that a compound which corresponds to the formula I but contains in place of H atoms one or more additional C—C and/or C—N and/or C—O bonds is reduced, or in that an amino keto acid derivative corresponds to the formula I but contains in place of a CH(NH$_2$) group a CO group is reductively aminated, or in that a carboxylic acid of the formula II $$X—G^1—OH \qquad\qquad II$$

in which
G$^1$ is
(a) Z$^1$,
(b) Z,
(c) Z—W,
(d) Z—W—B,
(e) Z—W—B—NR$^6$—CHR$^7$—CO— and
W is —NR$^2$—CHR$^3$—CHR$^4$—(CHR$^5$)$_n$—CO— is reacted with an amino compound of the formula III $$H—G^2 \qquad\qquad III$$

in which
G$^2$ is
(a) Z$^2$—W—B—D,
(b) W—B—D,
(c) B—D,
(d) D,
(e) —NH—(o—C$_6$H$_4$)—YH (in which it is also possible for one or more CH groups in the benzene ring to be replaced by N) and
Z$^1$ and Z$^2$ are together Z,
and in that, where appropriate, a functionally modified amino and/or hydroxyl group in a compound of the formula I is liberated by treatment with solvolyzing or hydrogenolyzing agents and/or a compound of the formula I is converted into one of its salts by treatment with an acid.

Moreover, the compounds of the formula I as well as the starting materials for their preparation are prepared by methods known per se, as described in the literature (for example in the standard works such as Houben-Weyl, Methoden der organischen Chemie (Methods of Organic Chemistry) published by Georg Thieme, Stuttgart; also European Pat. No. A-45665, European Pat. No. A-77028, European Pat. No. A-77029 and European Pat. No. A-81783), namely under reaction conditions which are known and suitable for the said reactions. It is also possible to make use of variants which are known per se but which are not mentioned here in detail for this purpose.

The starting materials can, if desired, also be formed in situ, so that they are not isolated from the reaction mixture but are immediately reacted further to give the compounds of the formula I.

The compounds of the formula i are preferably obtained by liberating them from their functional derivatives by solvolysis, in particular hydrolysis, or by hydrogenolysis.

Preferred starting materials for the solvolysis or hydrogenolysis are those which contain in place of one or more free amino and/or hydroxyl groups corresponding protected amino and/or hydroxyl groups, preferably those which carry in place of an H atom which is bonded to a N atom an amino protective group, for example those corresponding to the formula I, but contain in place of a His group a N(im)—$R^8$—His group (in which $R^8$ is an amino protective group, for example BOM or DNP), or those of the formula X—Z—NR$^2$—CHR$^3$—CH(NHR$^8$)—(CHR$^5$)$_n$—CO—B—D.

Starting materials which are also preferred are those which carry in place of the H atom of a hydroxyl group a hydroxyl protective group, for example those of the formula X—Z—NR$^2$—CHR$^3$—CHOR$^9$—(CHR$^5$)$_n$—CO—B—D, in which $R^9$ denotes a hydroxyl protective group.

It is also possible for several—identical or different—protected amino and/or hydroxyl groups to be present in the molecule of the starting material. If the protective groups which are present differ from one another, they can in many cases be eliminated selectively.

The term "amino protective group" is generally known and relates to groups which are suitable for protecting (blocking) an amino group from chemical reactions but which can readily be removed after the desired chemical reaction has been carried out elsewhere in the molecule. Typical groups of this type are, in particular, unsubstituted or substituted acyl, aryl (for example 2,4-dinitrophenyl), aralkoxymethyl (for example benzyloxymethyl) or aralkyl groups (for example benzyl, 4-nitrobenzyl or triphenylmethyl). Moreover, since the amino protective groups are removed after the desired reaction (or sequence of reactions), their nature and size is not critical; however, those which have 1-20, in particular 1-8, C atoms are preferred. The term "acyl group" in connection with the present process is to be understood in its widest sense. It embraces acyl groups derived from aliphatic, araliphatic, aromatic or heterocyclic carboxylic acids or sulfonic acids, as well as, in particular, alkoxycarbonyl, aryloxycarbonyl and, especially, aralkoxycarbonyl groups. Examples of acyl groups of these types are alkanoyl such as acetyl, propionyl, butyryl; aralkanoyl such as phenylacetyl; aroyl such as benzoyl or toluyl; aryloxyalkanoyl such as phenoxyacetyl; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methoxybenzyloxycarbonyl, FMOC. Preferred amino protective groups are DNP, BOM, CBZ, FMOC, benzyl and acetyl.

The term "hydroxyl protective group" is likewise generally known and relates to groups which are suitable to protect a hydroxyl group from chemical reactions which can readily be removed after the desired chemical reaction has been carried out elsewhere in the molecule. Typical groups of this type are the abovementioned unsubstituted or substituted aryl, aralkyl or acyl groups, as well as alkyl groups. The nature and size of the hydroxyl protective groups is not critical because they are removed again after the desired chemical reaction or sequence of reactions; groups which have 1-20, in particular 1-10, C atoms are preferred. Examples of hydroxyl protective groups are, inter alia, benzyl, p-nitrobenzoyl, p-toluenesulfonyl and acetyl, particular preference being given to benzyl and acetyl.

The functional derivatives of the compounds of the formula I which are to be used as starting materials can be prepared by customary methods of amino acid and peptide synthesis, as are described in, for example, the said standard works and patent specifications.

The liberation of the compounds of the formula I from their functional derivatives is effected—depending on the protective group used—for example with strong acids, preferably with trifluoracetic acid or perchloric acid, as well as with other strong inorganic acids such as hydrochloric acid or sulfuric acid, strong organic carboxylic acids such as trichloroacetic acid or sulfonic acids such as benzenesulfonic or p-toluenesulfonic acid. The presence of an additional inert solvent is possible but not always necessary. Inert solvents which are suitable and preferred are organic, for example carboxylic acids such as acetic acid, ethers such as tetrahydrofuran or dioxane, amides such as dimethylformamide (DMF), halogenated hydrocarbons such as dichloromethane, as well as alcohols such as methanol, ethanol or isopropanol, and water. Mixtures of the abovementioned solvents are also suitable. Trifluoroacetic acid is preferably used in excess without the addition of a further solvent, and perchloric acid is used in the form of a mixture of acetic acid and 70% perchloric acid in the ratio 9:1. The reaction temperatures for the cleavage are preferably between about 0° and about 50°, and it is preferably carried out between 15° and 30° (room temperature).

The BOC group can be eliminated, for example, preferably with 40% trifluoroacetic acid in methylene chloride or with about 3 to 5N HCl in dioxane at 15°-30°, and the FMOC group can be eliminated with an approximately 5 to 20% solution of dimethylamine, diethylamine or piperidine in DMF at 15°-30°. It is also possible to eliminate the DNP group with, for example, an approximately 3 to 10% solution of 2-mercaptoethanol in DMF/water at 15°-30°.

Protective groups which can be removed by hydrogenolysis (for example BOM, CBZ or benzyl) can be eliminated by, for example, treatment with hydrogen in the presence of a catalyst (for example a noble metal catalyst such as palladium, preferably on a support such as carbon). Solvents suitable for this purpose are the abovementioned, in particular, for example, alcohols such as methanol or ethanol, or amides such as DMF. The hydrogenolysis is, as a rule, carried out at temperatures between about 0° and 100° and under pressures between about 1 and 200 bar, preferably at 20-30° and under 1-10 bar. Satisfactory hydrogenolysis of the CBZ group takes place, for example, on 5 to 10% Pd-C in methanol at 20°-30°.

The compounds of the formula I can also be obtained by reduction of corresponding compounds which contain in place of H atoms one or more additional C—C and/or C—N and/or C—O bonds.

Thus, for example, keto compounds of the formula IV

$$X-Z-NR^2-CHR^3-CO-(CHR^5)_n-CO-B-D \quad IV$$

can be reduced to compounds of the formula I ($R^4=OH$), for example using a complex metal hydride such as $NaBH_4$, which does not simultaneously reduce the peptide carbonyl group, in an inert solvent such as methanol, at temperatures between about $-10°$ and $+30°$. The compounds of the formula IV (n=1) can be obtained by, for example, reaction of an amino acid of the formula $X-Z-NR^2-CHR^3-COOH$ with carbonyldiimidazole to give the corresponding imidazolide and subsequent reaction with malonic acid derivatives of the formula $HOOC-CHR^5-CO-B-D$ or their esters or salts, followed by decarboxylation.

The compounds of the formula I ($R^4=NH_2$) can also be prepared by reductive amination of corresponding amino keto acid derivatives, in particular those of the formula IV. The reductive amination can be carried out in one step or several steps. Thus, for example, the compound IV can be treated with ammonium salts, for example ammonium acetate, and $NaCNBH_3$, preferably in an inert solvent, for example an alcohol such as methanol, at temperatures between about 0° and 50°, in particular between 15° and 30°, and it is also possible initially to convert the keto compound IV into the oxime in the customary manner using hydroxylamine, and to reduce the latter to the amine, for example by catalytic hydrogenation or Raney nickel.

Compounds of the formula I can also be obtained by direct peptide synthesis from a carboxylic acid and an amine component. Examples of suitable carboxylic acid components are those of the part-formulae $X-Z-OH$, $X-Z-W-OH$ or $X-Z-W-B-NR^6-CHR^7-COOH$, and of amine components are those of the part-formulae $H-W-B-D$, $H-W-B$ or $o-H_2N-C_6H_4-YH$. The peptide bond can, however, also be formed inside the group Z; this entails reaction of a carboxylic acid of the formula $X-Z^1-OH$ with an aminopeptide of the formula $H-Z^2-W-B-D$, $Z^1+Z^2$ being Z. This is preferably carried out by customary methods of peptide synthesis as are described in, for example, Houben-Weyl, loc. cit., volume 15/II, pages 1 to 806 (1974).

The reaction is preferably effected in the presence of a dehydrating agent, for example of a carbodiimide such as DCCI or dimethylaminopropylethylcarbodimide, as well as propanephosphonic anhydride (compare Angew. Chem. 92, 129 (1980)), diphenylphosphoryl azide or 2-ethoxy-N-ethoxycarbonyl-1,2-dihydroquinoline, in an inert solvent, for example a halogenated hydrocarbon such as dichloromethane, an ether such as tetrahydrofuran or dioxane, an amide such as DMF or dimethylacetamide, or a nitrile such as acetonitrile, at temperatures between about $-10$ and 40, preferably between 0° and 30°.

It is also possible to use in the reaction in place of II or III suitable reactive derivatives of these substances, for example those in which there has been intermediate blockage of reactive groups by protective groups. The amino acid derivatives III can be used in the form of, for example, their activated esters, which are preferably formed in situ, for example by addition of 1-hydroxybenzotriazole or N-hydroxysuccinimide.

Most of the starting materials of the formulae II and III are known. Where they are unknown, they can be prepared by known methods, for example the abovementioned methods of peptide synthesis and of elimination of protective groups.

If desired, a functionally modified amino and/or hydroxyl group in a compound of the formula I can be liberated by solvolysis or hydrogenolysis by one of the methods described above.

Thus, in particular, a compound of the formula I in which X is different from H can be converted into a compound of the formula I (X=H), preferably by hydrogenolysis if X is CBZ, otherwise by selective solvolysis. If X is BOC, it is possible to eliminate the BOC group with, for example, HCl in dioxane at room temperature.

A base of the formula I can be converted into the relevant acid addition salt with an acid. Particularly suitable acids for this reaction are those which provide physiologically acceptable salts. Thus, it is possible to use inorganic acids, for example sulfuric acid, nitric acid, hydrohalic acids such as hydrochloric acid or hydrobromic acid, phosphoric acids such as orthophosphoric acid, sulfamic acid, as well as organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and -disulfonic acids, and laurylsulfuric acid. Salts with physiologically unacceptable acids, for example picrates, can be used to isolate and/or purify the compounds of the formula I.

The new compounds of the formula I and their physiologically acceptable salts can be used for the preparation of pharmaceutical products by converting them into a suitable dosage form together with at least one vehicle or auxiliary and, if desired, together with one or more other active compound(s). The formulations thus obtained can be used as medicaments in human or veterinary medicine. Suitable vehicles are organic or inorganic substances which are suitable for enteral (for example oral or rectal) or parenteral administration or for administration in the form of an inhalation spray and which do not react with the new compounds, for example water, vegetable oils, benzyl alcohols, polyethylene glycols, glycerol triacetate and other fatty acid glycerides, gelatin, soya lecithin, carbohydrates such as lactose or starch, magnesium stearate, talc, cellulose. In particular, tablets, coated tablets, capsules, syrups, juices or drops are used for oral administration; coated tablets and capsules with coatings resistant to gastric juice are of special interest.

Suppositories are used for rectal administration, and solutions, preferably oily or aqueous solutions, as well as suspensions, emulsions or implants are used for parenteral administration. For administration as inhalation spray it is possible to use sprays which contain the active compound either dissolved or suspended in a propellant gas mixture (for example fluoro-chloro-hydrocarbons). The active compound is preferably used in micronized form for this purpose, it being possible for one or more additional physiologically tolerated solvents to be present, for example ethanol. Inhalation solutions can be administered with the aid of customary inhalers. The new compounds can also be freeze-dried, and the resulting lyophilisates used, for example, for the preparation of injection products. The abovementioned formulations can be sterilized and/or contain auxiliaries such as preservatives, stabilizers and/or wetting agents, emulsifiers, salts to influence the osmotic pressure, buffer substances, colorants and/or flavourings. They can, if desired, also contain one or more other active compounds, for example one or more vitamins.

The substances according to the invention are, as a rule, administered in analogy to other known and commercially available peptides, but in particular in analogy to the compounds described in European Patent A-77028, preferably in doses between about 100 mg and 30 g, in particular between 500 mg and 5 g, per dose unit. The daily dose is preferably between about 2 and 600 mg/kg of body weight. However, the specific dose for each particular patient depends on a wide variety of factors, for example on the efficacy of the specific compound used, on the age, body weight, general state of health, sex, on the diet, on the time and route of administration, on the rate of excretion, the pharmaceutical combination and the severity of the particular disease to which the therapy is applied. Parenteral administration is preferred.

Renin-associated hypertension and hyperaldosteronism are effectively treated by administration of from 10 to 300 mg/kg of body weight. For diagnostic purposes, the novel peptides may be administered in a single dose of from 0.1 to 10 mg/kg of body weight.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

In the examples which follow, "usual working up" means: if necessary, water is added, and the mixture is neutralized, extracted with ether or dichloromethane, the organic phase is separated off, dried over sodium sulfate, filtered and evaporated, and the residue is purified by chromatography on silica gel and/or crystallization.

EXAMPLES

Example 1

A mixture of 400 mg of 2- [1S-(3S-hydroxy-4S-(N-tert.-butoxycarbonyl-L-phenylalanyl-N(im)-(2,4-dinitrophenyl)-L-histidylamino)-5-cyclohexylpen-tanoylamino)-3-methylbutyl]benzimidazole ["2-(1S-BOC-Phe-imi-DNP-His-AHCP-amino-3-methylbutyl)-benzimidazole"; m.p. 130° (decomposition); obtainable by reaction of BOC-Ile-OH with o-phenylenediamine to give N-BOC-ILe-o-phenylenediamine, cyclization with acetic acid (5 h at 65°) to give 2-(1S-BOC-amino-3-methylbutyl)-benzimidazole (m.p. 211°–213°), elimination of the BOC group with 4N HCl indioxane to give 2-(1S-amino-3-methylbutyl)benzimidazole (m.p. 240°–242° (decomposition), reaction with BOC-AHCP-OH/DCCI/HOBt to give 2-(1S-BOC-AHCP-amino-3-methylbutyl)benzimidazole (m.p. 180°–182°), elimination of the BOC group and condensation with BOC-imi-DNP-His-OH to give 2-(1S-BOC-imi-DNP-His-AHCP-amino-3-methylbutyl)benzimidazole (m.p. 140°, decomposition), renewed elimination of the BOC group and reaction with BOC-Phe-OH], 860 mg of 2-mercaptoethanol, 10 ml of DMF and 10 ml of water is stirred at 20°, adjusted to pH 8 with aqueous $Na_2CO_3$ solution and stirred at 20° for 2 h. After the usual working up, 2-[1S-(3S-hydroxy-4S-(N-tert.-butoxycarbonyl-L-phenylalanyl-L-histidyl-amino)-5-cyclohexylpen-tanoylamino)-3-methylbutyl]benzimidazole ["2-(1S-BOC-Phe-His-AHCP-amino-3-methylbutyl)ben-zimidazole"] is obtained, m.p. 140° (decomposition).

The following are obtained analogously by cleavage of the corresponding imi-DNP derivatives:

2-(BOC-His-AHCP-aminomethyl)-benzimidazole
2-(1S-BOC-His-AHCP-aminoethyl)-benzimidazole
2-(1S-BOC-His-AHCP-aminopropyl)-benzimidazole
2-(1S-BOC-His-AHCP-aminobutyl)-benzimidazole
2-(1S-BOC-His-AHCP-amino-2-methylbutyl)-benzimidazole
2-(1S-BOC-His-AHCP-amino-3-methylbutyl)-benzimidazole
2-(BOC-Phe-His-AHCH-aminomethyl)-benzimidazole
2-(BOC-Phe-His-Sta-aminomethyl)-benzimidazole
2-(BOC-Phe-His-AHPP-aminomethyl)-benzimidazole
2-(BOC-Phe-His-DACP-aminomethyl)-benzimidazole
2-(BOC-Phe-His-DACH-aminomethyl)-benzimidazole
2-(BOC-Phe-His-DAMH-aminomethyl)-benzimidazole
2-(BOC-Phe-His-DAPP-aminomethyl)-benzimidazole
2-(POA-His-AHCP-aminomethyl)-benzimidazole
2-(4-Phenylbutyryl-His-AHCP-aminomethyl)-benzimidazole
2-(2-Benzyl-3-phenylpropionyl-His-AHCP-aminomethyl)-benzimidazole
2-(2-Benzyl-4-phenylbutyryl-His-AHCP-aminomethyl)-benzimidazole
2-[2-Phenylethyl)-4-phenylbutyryl-His-AHCP-aminomethyl]-benzimidazole
2-[2-(2-Naphthylmethyl)-4-phenylbutyryl-His-AHCP-aminomethyl]-benzimidazole
2-(1S-POA-His-AHCP-amino-3-methylbutyl)-benzimidazole
2-[1S-(4-Phenylbutyryl-His-AHCP-amino)-3-methylbutyl]-benzimidazole
2-[1S-(2-Benzyl-3-phenylpropionyl-His-AHCP-amino)-3-methylbutyl]-benzimidazole
2-[1S-(2-Benzyl-4-phenylbutyryl-His-AHCP-amino)-3-methylbutyl]-benzimidazole, m.p. 130°
2-[1S-(2-(2-phenylethyl)-4-phenylbutyryl-His-AHCP-amino)-3-methylbutyl]-benzimidazole
2-[1S-(2-(2-Napthylmethyl)-4-phenylbutyryl-His-AHCP-amino)-3-methylbutyl]-benzimidazole
2-(POA-His-AHCP-Ile-aminomethyl)-benzimidazole
2-(4-Phenylbutyryl-His-AHCP-Ile-aminomethyl)-benzimidazole
2-(2-Benzyl-3-phenylpropionyl-His-AHCP-Ile-aminomethyl)-benzimidazole
2-(2-Benzyl-4-phenylbutyryl-His-AHCP-Ile-aminomethyl)-benzimidazole 2-(2-Benzyl-4-phenylbutyryl-His-AHCP-Ile-aminomethyl)-1H-imidazo[4,5-b]pyridine
2-(2-Benzyl-4-phenylbutyryl-His-AHCP-Ile-aminomethyl)-1H-imidazo[4,5-c]pyridine
2-[2-(2-Phenylethyl)-4-phenylbutyryl-His-AHCP-Ile-aminomethyl]-benzimidazole
2-[2-(2-Naphthylmethyl)-4-phenylbutyryl-His-AHCP-Ile-aminomethyl]-benzimidazole
2-(1S-POA-His-AHCP-Ile-amino-3-methylbutyl)-benzimidazole
2-[1S-(4-Phenylbutyryl-His-AHCP-Ile-amino)-3-methylbutyl]-benzimidazole
2-[1S-(2-Benzyl-3-phenylpropionyl-His-AHCP-Ile-amino)-3-methylbutyl]-benzimidazole
2-[1S-(2-Benzyl-4-phenylbutyryl-His-AHCP-Ile-amino)-3-methylbutyl]-benzimidazole
2-[1S-(2-(2-Phenylethyl)-4-phenylbutyryl-His-AHCP-Ile-amino)-3-methylbutyl]-benzimidazole
2-[1S-(2-(2-Naphthylmethyl)-4-phenylbutyryl-His-AHCP-Ile-amino)-3-methylbutyl]-benzimidazole
2-(2-Benzyl-4-phenylbutyryl-His-AHcP-Leu-aminomethyl)-benzimidazole
2-(2-Benzyl-4-phenylbutyryl-His-AHCP-Leu-aminomethyl)-1H-imidazo[4,5-b]pyridine
2-(2-Benzyl-4-phenylbutyryl-His-AHCP-Leu-aminomethyl)-1H-imidazo[4,5-c]pyridine
2-[1S-(2-Benzyl-4-phenylbutyryl-His-AHCP-Leu-amino)-3-methylbutyl]-benzimidazole
2-(BOC-Abu-His-AHCP-aminomethyl)-benzimidazole
2-(BOC-Ada-His-AHCP-aminomethyl)-benzimidazole
2-(BOC-Ala-His-AHCP-aminomethyl)-benzimidazole
2-(BOC-Arg-His-AHCP-aminomethyl)-benzimidazole
2-(BOC-Asn-His-AHCP-aminomethyl)-benzimidazole
2-(BOC-Bia-His-AHCP-aminomethyl)-benzimidazole
2-(BOC-Cal-His-AHCP-aminomethyl)-benzimidazole
2-(BOC-Dab-His-AHCP-aminomethyl)-benzimidazole
2-(BOC-Gln-His-AHCP-aminomethyl)-benzimidazole
2-(BOC-Gly-His-AHCP-aminomethyl)-benzimidazole
2-(BOC-His-His-AHCP-aminomethyl)-benzimidazole
2-(BOC-N(im)-methyl-His-His-AHCP-aminomethyl)-benzimidazole
2-(BOC-Ile-His-AHCP-aminomethyl)-benzimidazole
2-(BOC-Leu-His-AHCP-aminomethyl)-benzimidazole
2-(BOC-tert.-Leu-His-AHCP-aminomethyl)-benzimidazole
2-(BOC-Lys-His-AHCP-aminomethyl)-benzimidazole
2-(BOC-Met-His-AHCP-aminomethyl)-benzimidazole
2-(BOC-αNal-His-AHCP-aminomethyl)-benzimidazole
2-(BOC-βNal-His-AHCP-aminomethyl)-benzimidazole
2-(BOC-Nbg-His-AHCP-aminomethyl)-benzimidazole
2-(BOC-Nle-His-AHCP-aminomethyl)-benzimidazole
2-(BOC-Orn-His-AHCP-aminomethyl)-benzimidazole
2-(BOC-Pro-His-AHCP-aminomethyl)-benzimidazole
2-(BOC-Ser-His-AHCP-aminomethyl)-benzimidazole
2-(BOC-Thr-His-AHCP-aminomethyl)-benzimidazole
2-(BOC-Tic-His-AHCP-aminomethyl)-benzimidazole
2-(BOC-Trp-His-AHCP-aminomethyl)-benzimidazole
2-(BOC-Tyr-His-AHCP-aminomethyl)-benzimidazole
2-(BOC-Val-His-AHCP-aminomethyl)-benzimidazole
2-(1S-BOC-Abu-His-AHCP-amino-3-methylbutyl)-benzimidazole
2-(1S-BOC-Ada-His-AHCP-amino-3-methylbutyl)-benzimidazole
2-(1S-BOC-Ala-His-AHCP-amino-3-methylbutyl)-benzimidazole
2-(1S-BOC-Arg-His-AHCP-amino-3-methylbutyl)-benzimidazole
2-(1S-BOC-Asn-His-AHCP-amino-3-methylbutyl)-benzimidazole
2-(1S-BOC-Bia-His-AHCP-amino-3-methylbutyl)-benzimidazole
2-(1S-BOC-Cal-His-AHCP-amino-3-methylbutyl)-benzimidazole
2-(1S-BOC-Dab-His-AHCP-amino-3-methylbutyl)-benzimidazole
2-(1S-BOC-Gln-His-AHCP-amino-3-methylbutyl)-benzimidazole
2-(1S-BOC-Gly-His-AHCP-amino-3-methylbutyl)-benzimidazole
2-(1S-BOC-His-His-AHCP-amino-3-methylbutyl)-benzimidazole
2-(1S-BOC-N(im)-methyl-His-His-AHCP-amino-3-methylbutyl)-benzimidazole
2-(1S-BOC-Ile-His-AHCP-amino-3-methylbutyl)-benzimidazole
2-(1S-BOC-Leu-His-AHCP-amino-3-methylbutyl)-benzimidazole
2-(1S-BOC-tert.-Leu-His-AHCP-amino-3-methylbutyl)-benzimidazole
2-(1S-BOC-Lys-His-AHCP-amino-3-methylbutyl)-benzimidazole
2-(1S-BOC-Met-His-AHCP-amino-3-methylbutyl)-benzimidazole
2-(1S-BOC-αNal-His-AHCP-amino-3-methylbutyl)-benzimidazole
2-(1S-BOC-βNal-His-AHCP-amino-3-methylbutyl)-benzimidazole
2-(1S-BOC-Nbg-His-AHCP-amino-3-methylbutyl)-benzimidazole
2-(1S-BOC-Nle-His-AHCP-amino-3-methylbutyl)-benzimidazole
2-(1S-BOC-Orn-His-AHCP-amino-3-methylbutyl)-benzimidazole
2-(1S-BOC-Pro-His-AHCP-amino-3-methylbutyl)-benzimidazole
2-(1S-BOC-Ser-His-AHCP-amino-3-methylbutyl)-benzimidazole
2-(1S-BOC-Thr-His-AHCP-amino-3-methylbutyl)-benzimidazole
2-(1S-BOC-Tic-His-AHCP-amino-3-methylbutyl)-benzimidazole
2-(1S-BOC-Trp-His-AHCP-amino-3-methylbutyl)-benzimidazole
2-(1S-BOC-Tyr-His-AHCP-amino-3-methylbutyl)-benzimidazole
2-(1S-BOC-Val-His-AHCP-amino-3-methylbutyl)-benzimidazole
2-(BOC-Abu-His-AHCP-Ile-aminomethyl)-benzimidazole
2-(BOC-Ada-His-AHCP-Ile-aminomethyl)-benzimidazole
2-(BOC-Ala-His-AHCP-Ile-aminomethyl)-benzimidazole
2-(BOC-Arg-His-AHCP-Ile-aminomethyl)-benzimidazole
2-(BOC-Asn-His-AHCP-Ile-aminomethyl)-benzimidazole
2-(BOC-Bia-His-AHCP-Ile-aminomethyl)-benzimidazole
2-(BOC-Cal-His-AHCP-Ile-aminomethyl)-benzimidazole
2-(BOC-Dab-His-AHCP-Ile-aminomethyl)-benzimidazole
2-(BOC-Gln-His-AHCP-Ile-aminomethyl)-benzimidazole 2-(BOC-Gly-His-AHCP-Ile-aminomethyl)-benzimidazole
2-(BOC-His-His-AHCP-Ile-aminomethyl)-benzimidazole
2-(BOC-N(im)-methyl-His-His-AHCP-Ile-aminomethyl)-benzimidazole
2-(BOC-Ile-His-AHCP-Ile-aminomethyl)-benzimidazole
2-BOC-Leu-His-AHCP-Ile-aminomethyl)-benzimidazole
2-(BOC-tert.-Leu-His-AHCP-Ile-aminomethyl)-benzimidazole
2-(BOC-Lys-His-AHCP-Ile-aminomethyl)-benzimidazole
2-(BOC-Met-His-AHCP-Ile-aminomethyl)-benzimidazole
2-(BOC-αNal-His-AHCP-Ile-aminomethyl)-benzimidazole
2-(BOC-βNal-His-AHCP-Ile-aminomethyl)-benzimidazole
2-(BOC-Nbg-His-AHCP-Ile-aminomethyl)-benzimidazole
2-(BOC-Nle-His-AHCP-Ile-aminomethyl)-benzimidazole
2-(BOC-Orn-His-AHCP-Ile-aminomethyl)-benzimidazole
2-(BOC-Pro-His-AHCP-Ile-aminomethyl)-benzimidazole
2-(BOC-Ser-His-AHCP-Ile-aminomethyl)-benzimidazole
2-(BOC-Thr-His-AHCP-Ile-aminomethyl)-benzimidazole
2-(BOC-Tic-His-AHCP-Ile-aminomethyl)-benzimidazole
2-(BOC-Trp-His-AHCP-Ile-aminomethyl)-benzimidazole
2-(BOC-Tyr-His-AHCP-Ile-aminomethyl)-benzimidazole
2-(BOC-Val-His-AHCP-Ile-aminomethyl)-benzimidazole
2-(1S-BOC-Abu-His-AHCP-Ile-amino-3-methylbutyl)-benzimidazole
2-(1S-BOC-Ada-His-AHCP-Ile-amino-3-methylbutyl)-benzimidazole
2-(1S-BOC-Ala-His-AHCP-Ile-amino-3-methylbutyl)-benzimidazole
2-(1S-BOC-Arg-His-AHCP-Ile-amino-3-methylbutyl)-benzimidazole
2-(1S-BOC-Asn-His-AHCP-Ile-amino-3-methylbutyl)-benzimidazole
2-(1S-BOC-Bia-His-AHCP-Ile-amino-3-methylbutyl)-benzimidazole
2-(1S-BOC-Cal-His-AHCP-Ile-amino-3-methylbutyl)-benzimidazole
2-(1S-BOC-Dab-His-AHCP-Ile-amino-3-methylbutyl)-benzimidazole
2-(1S-BOC-Gln-His-AHCP-Ile-amino-3-methylbutyl)-benzimidazole
2-(1S-BOC-Gly-His-AHCP-Ile-amino-3-methylbutyl)-benzimidazole
2-(1S-BOC-His-His-AHCP-Ile-amino-3-methylbutyl)-benzimidazole
2-(1S-BOC-N(im)-methyl-His-His-AHCP-Ile-amino-3-methylbutyl)-benzimidazole
2-(1S-BOC-Ile-His-AHCP-Ile-amino-3-methylbutyl)-benzimidazole
2-(1S-BOC-Leu-His-AHCP-Ile-amino-3-methylbutyl)-benzimidazole
2-(1S-BOC-tert.-Leu-His-AHCP-Ile-amino-3-methylbutyl)-benzimidazole
2-(1S-BOC-Lys-His-AHCP-Ile-amino-3-methylbutyl)-benzimidazole
2-(1S-BOC-Met-His-AHCP-Ile-amino-3-methylbutyl)-benzimidazole
2-(1S-BOC-αNal-His-AHCP-Ile-amino-3-methylbutyl)-benzimidazole
2-(1S-BOC-βNal-His-AHCP-Ile-amino-3-methylbutyl)-benzimidazole
2-(1S-BOC-Nbg-His-AHCP-Ile-amino-3-methylbutyl)-benzimidazole
2-(1S-BOC-Nle-His-AHCP-Ile-amino-3-methylbutyl)-benzimidazole
2-(1S-BOC-Orn-His-AHCP-Ile-amino-3-methylbutyl)-benzimidazole
2-(1S-BOC-Pro-His-AHCP-Ile-amino-3-methylbutyl)-benzimidazole
2-(1S-BOC-Ser-His-AHCP-Ile-amino-3-methylbutyl)-benzimidazole
2-(1S-BOC-Thr-His-AHCP-Ile-amino-3-methylbutyl)-benzimidazole
2-(1S-BOC-Tic-His-AHCP-Ile-amino-3-methylbutyl)-benzimidazole
2-(1S-BOC-Trp-His-AHCP-Ile-amino-3-methylbutyl)-benzimidazole
2-(1S-BOC-Tyr-His-AHCP-Ile-amino-3-methylbutyl)-benzimidazole
2-(1S-BOC-Val-His-AHCP-Ile-amino-3-methylbutyl)-benzimidazole
2-(BOC-Phe-His-AHCP-Abu-aminomethyl)-benzimidazole
2-(BOC-Phe-His-AHCP-Ala-aminomethyl)-benzimidazole
2-(BOC-Phe-His-AHCP-Cal-aminomethyl)-benzimidazole
2-(BOC-Phe-His-AHCP-Gly-aminomethyl)-benzimidazole
2-(BOC-Phe-His-AHCP-Leu-aminomethyl)-benzimidazole
2-(BOC-Phe-His-AHCP-Leu-aminomethyl)-1H-imidazo[4,5-b]pyridine, sinters at 165°–170°
2-(BOC-Phe-His-AHCP-Leu-aminomethyl)-1H-imidazo[4,5-c]pyridine, sinters at 110°–115°
2-(BOC-Phe-His-AHCP-Met-aminomethyl)-benzimidazole
2-(BOC-Phe-His-AHCP-Nle-aminomethyl)-benzimidazole
2-(BOC-Phe-His-AHCP-Val-aminomethyl)-benzimidazole
2-(1S-BOC-Phe-His-AHCP-Abu-amino-3-methylbutyl)-benzimidazole
2-(1S-BOC-Phe-His-AHCP-Ala-amino-3-methylbutyl)-benzimidazole
2-(1S-BOC-Phe-His-AHCP-Cal-amino-3-methylbutyl)-benzimidazole
2-(1S-BOC-Phe-His-AHCP-Gly-amino-3-methylbutyl)-benzimidazole
2-(1S-BOC-Phe-His-AHCP-Leu-amino-3-methylbutyl)-benzimidazole
2-(1S-BOC-Phe-His-AHCP-Leu-amino-3-methylbutyl)-1H-imidazo[4,5-b]pyridine
2-(1S-BOC-Phe-His-AHCP-Leu-amino-3-methylbutyl)-1H-imidazo[4,5-c]pyridine
2-(1S-BOC-Phe-His-AHCP-Met-amino-3-methylbutyl)-benzimidazole
2-(1S-BOC-Phe-His-AHCP-Nle-amino-3-methylbutyl)-benzimidazole 2-(1S-BOC-Phe-His-AHCP-Val-amino-3-methylbutyl)-
   benzimidazole
2-(BOC-Phe-His-AHCP-aminomethyl)-benzimidazole,
   formate m.p. 201° (decomposition)
2-(BOC-Phe-His-AHCP-aminomethyl)-1H-
   imidazo[4,5-b]pyridine, sinters at 185°-195°
2-(BOC-Phe-His-AHCP-aminomethyl)-1H-
   imidazo[4,5-c]pyridine, sinters at 165°-170°
2-(1S-BOC-Phe-His-AHCP-aminoethyl)-benzimidazole
2-(1S-BOC-Phe-His-AHCP-aminopropyl)-ben-
   zimidazole
2-(1S-BOC-Phe-His-AHCP-aminobutyl)-benzimidazole
2-(1S-BOC-Phe-His-AHCP-amino-2-methylbutyl)-ben-
   zimidazole
2-(1S-BOC-Phe-His-AHCP-amino-3-methylbutyl)-1H-
   imidazo[4,5-b]pyridine, sinters at 130°-135°
2-(1S-BOC-Phe-His-AHCP-amino-3-methylbutyl)-1H-
   imidazo[4,5-c]pyridine
2-(1S-BOC-Phe-His-AHCP-amino-3-methylbutyl)-ben-
   zoxazole
2-(1S-BOC-Phe-His-AHCP-amino-3-methylbutyl)-
   benzthiazole
2-(BOC-Phe-His-AHCP-Ile-aminomethyl)-ben-
   zimidazole, m.p. 213° (decomposition)
2-(BOC-Phe-His-AHCP-Ile-aminomethyl)-1H-
   imidazo[4,5-b]pyridine
2-(BOC-Phe-His-AHCP-Ile-aminomethyl)-1H-
   imidazo[4,5-c]pyridine
2-(1S-BOC-Phe-His-AHCP-Ile-aminoethyl)-ben-
   zimidazole
2-(1S-BOC-Phe-His-AHCP-Ile-aminopropyl)-ben-
   zimidazole
2-(1S-BOC-Phe-His-AHCP-Ile-aminobutyl)-ben-
   zimidazole
2-(1S-BOC-Phe-His-AHCP-Ile-amino-2-methylbutyl)-
   benzimidazole
2-(1S-BOC-Phe-His-AHCP-Ile-amino-3-methylbutyl)-
   benzimidazole, m.p. 166°-168°
2-(1S-BOC-Phe-His-AHCP-Ile-amino-3-methylbutyl)-
   1H-imidazo[4,5-b]pyridine
2-(1S-BOC-Phe-His-AHCP-Ile-amino-3-methylbutyl)-
   1H-imidazo[4,5-c]pyridine
2-(1S-BOC-Phe-His-AHCP-Ile-amino-3-methylbutyl)-
   benzoxazole
2-(1S-BOC-Phe-His-AHCP-Ile-amino-3-methylbutyl)-
   benzthiazole Example 2

1 g of 2-(1S-BOC-Phe-imi-BOM-His-AHCP-amino-3-methylbutyl)benzimidazole [obtainable from 2-(1S-AHCP-amino-3-methylbutyl)benzimidazole by condensation with BOC-Phe-imi-BOM-His-OH] is dissolved in 10 ml of methanol, hydrogenated on 0.5 g of 10% Pd-C at 20° and under 1 bar for 3 h, and the mixture is filtered, the filtrate is evaporated, and 2-(1S-BOC-Phe-His-AHCP-amino-3-methylbutyl)benzimidazole is obtained, m.p. 140° (decomposition).

The compounds in Example 1 are obtained analogously from the corresponding imi-BOM derivatives.

Example 3

A solution of 782 mg of 2-[1S-(3-oxo-4S-BOC-Phe-His-amino-5-cyclohexylpentanoylamino)-3-methylbutyl]benzimidazole and 1.43 g of Na₂CO₃.10H₂O in 5 ml of methanol and 5 ml of water is mixed with 70 mg of hydroxylamine hydrochloride and stirred at 20° for 14 h. The precipitated oxime is filtered off, dried, dissolved in 10 ml of methanol and hydrogenated on 0.5 g of Raney Ni at 20° and under 5 bar. The catalyst is removed by filtration, the filtrate is evaporated, and separation is carried out on silica gel (dichloromethane/methanol/acetic acid/water) and 2-[1S-(3S-amino-4S-BOC-Phe-His-amino-5-cyclohexylpentanoylamino)-3-methylbutyl]benzimidazole ["2-(1S-BOC-Phe-His-DACP-amino-3-methylbutyl)benzimidazole"] is obtained; the 3R-amino epimer is also obtained.

Example 4

A solution of 4 g of 2-(1S-AHCP-amino-3-methylbutyl)benzimidazole in 60 ml of dichloromethane is mixed with 1.01 g of N-methylmorpholine. While stirring, 3.78 g of BOC-Phe-Nle-OH, 1.35 g of HOBt and a solution of 2.06 g of DCCI in 50 ml of dichloromethane are added, and the mixture is stirred at 4° for 14 h, the precipitated dicyclohexylurea is removed by filtration, and the filtrate is evaporated. The usual working up is carried out and 2-(1S-BOC-Phe-Nle-AHCP-amino-3-methylbutyl)benzimidazole is obtained.

The following are obtained analogously from the corresponding BOC-dipeptides and 2-(1S-H-AHCP-Ile-amino-3-methylbutyl)benzimidazole:
2-(1S-BOC-Phe-Abu-AHCP-Ile-amino-3-methylbutyl)-
   benzimidazole
2-(1S-BOC-Phe-Ada-AHCP-Ile-amino-3-methylbutyl)-
   benzimidazole
2-(1S-BOC-Phe-Ala-AHCP-Ile-amino-3-methylbutyl)-
   benzimidazole
2-(1S-BOC-Phe-Bia-AHCP-Ile-amino-3-methylbutyl)-
   benzimidazole
2-(1S-BOC-Phe-Cal-AHCP-Ile-amino-3-methylbutyl)-
   benzimidazole
2-(1S-BOC-Phe-Gly-AHCP-Ile-amino-3-methylbutyl)-
   benzimidazole
2-(1S-BOC-Phe-N(im)-methyl-His-AHCP-Ile-amino-3-
   methylbutyl)-benzimidazole
2-(1S-BOC-Phe-Ile-AHCP-Ile-amino-3-methylbutyl)-
   benzimidazole
2-(1S-BOC-Phe-Leu-AHCP-Ile-amino-3-methylbutyl)-
   benzimidazole
2-(1S-BOC-Phe-tert.-Leu-AHCP-Ile-amino-3-methyl-
   butyl)-benzimidazole
2-(1S-BOC-Phe-Met-AHCP-Ile-amino-3-methylbutyl)-
   benzimidazole
2-(1S-BOC-Phe-α-Nal-AHCP-Ile-amino-3-methyl-
   butyl)-benzimidazole
2-(1S-BOC-Phe-β-Nal-AHCP-Ile-amino-3-methyl-
   butyl)-benzimidazole
2-(1S-BOC-Phe-Nbg-AHCP-Ile-amino-3-methylbutyl)-
   benzimidazole
2-(1S-BOC-Phe-Nle-AHCP-Ile-amino-3-methylbutyl)-
   benzimidazole
2-(1S-BOC-Phe-Pro-AHCP-Ile-amino-3-methylbutyl)-
   benzimidazole
2-(1S-BOC-Phe-Ser-AHCP-Ile-amino-3-methylbutyl)-
   benzimidazole
2-(1S-BOC-Phe-Thr-AHCP-Ile-amino-3-methylbutyl)-
   benzimidazole
2-(1S-BOC-Phe-Tic-AHCP-Ile-amino-3-methylbutyl)-
   benzimidazole
2-(1S-BOC-Phe-Trp-AHCP-Ile-amino-3-methylbutyl)-
   benzimidazole
2-(1S-BOC-Phe-Val-AHCP-Ile-amino-3-methylbutyl)-
   benzimidazole.

Example 5

2-(BOC-Phe-Nle-AHCP-aminomethyl)-benzimidazole is obtained in analogy to Example 4 from BOC-Phe-OH and 2-(Nle-AHCP-aminomethyl)benzimidazole (obtainable by reaction of BOC-Gly-OH with o-phenylenediamine to give 2-BOC-aminomethylbenzimidazole, elimination of the BOC group, condensation with BOC-Nle-AHCP-OH to give 2-BOC-Nle-AHCP-aminomethylbenzimidazole and renewed elimination of the BOC group).

Example 6

2-(1S-BOC-Phe-Nle-AHCP-Ile-amino-3-methylbutyl)-benzimidazole is obtained in analogy in Example 4 from BOC-Phe-Nle-AHCP-OH and 2-(1S-Ile-amino-3-methylbutyl)-benzimidazole.

Example 7

2-(1S-BOC-Phe-Nle-AHCP-Ile-amino-3-methylbutyl)-benzimidazole is obtained in analogy to Example 4 from BOC-Phe-Nle-AHCP-Ile-OH and 2-(1S-amino-3-methylbutyl)-benzimidazole.

Example 8

2-(1S-BOC-Phe-Nle-AHCP-Ile-Amino-3-methylbutyl)-benzimidazole is obtained in analogy to Example 4 from BOC-Phe-Nle-AHCP-Ile-Leu-OH and o-phenylenediamine.

Example 9

A solution of 1 g of 2-(1S-BOC-Phe-His-AHCP-amino-3-methylbutyl)benzimidazole in 20 ml of 4N HCl in dixoane is stirred at 20° for 30 min and then evaporated. 2-(1S-H-Phe-His-AHCP-amino-3-methylbutyl)-benzimidazole is obtained.

The following are obtained analogously by cleavage of the corresponding N-BOC derivatives:

2-(H-His-AHCP-aminomethyl)-benzimidazole
2-(1S-H-His-AHCP-aminoethyl)-benzimidazole
2-(1S-H-His-AHCP-aminopropyl)-benzimidazole
2-(1S-H-His-AHCP-aminobutyl)-benzimidazole
2-(1S-H-His-AHCP-amino-2-methylbutyl)-benzimidazole
2-(1S-H-His-AHCP-amino-3-methylbutyl)-benzimidazole
2-(H-Phe-His-AHCH-aminomethyl)-benzimidazole
2-(H-Phe-His-Sta-aminomethyl)-benzimidazole
2-(H-Phe-His-AHPP-aminomethyl)-benzimidazole
2-(H-Phe-His-DACP-aminomethyl)-benzimidazole
2-(H-Phe-His-DACH-aminomethyl)-benzimidazole
2-(H-Phe-His-DAMH-aminomethyl)-benzimidazole
2-(H-Phe-His-DAPP-aminomethyl)-benzimidazole
2-(H-Abu-His-AHCP-aminomethyl)-benzimidazole
2-(H-Ada-His-AHCP-aminomethyl)-benzimidazole
2-(H-Ala-His-AHCP-aminomethyl)-benzimidazole
2-(H-Arg-His-AHCP-aminomethyl)-benzimidazole
2-(H-Asn-His-AHCP-aminomethyl)-benzimidazole
2-(H-Bia-His-AHCP-aminomethyl)-benzimidazole
2-(H-Cal-His-AHCP-aminomethyl)-benzimidazole
2-(H-Dab-His-AHCP-aminomethyl)-benzimidazole
2-(H-Gln-His-AHCP-aminomethyl)-benzimidazole
2-(H-Gly-His-AHCP-aminomethyl)-benzimidazole
2-(H-His-His-AHCP-aminomethyl)-benzimidazole
2-(H-N(im)-methyl-His-His-AHCP-aminomethyl)-benzimidazole
2-(H-Ile-His-AHCP-aminomethyl)-benzimidazole
2-(H-Leu-His-AHCP-aminomethyl)-benzimidazole
2-(H-tert.-Leu-His-AHCP-aminomethyl)-benzimidazole
2-(H-Lys-His-AHCP-aminomethyl)-benzimidazole
2-(H-Met-His-AHCP-aminomethyl)-benzimidazole
2-(H-αNal-His-AHCP-aminomethyl)-benzimidazole
2-(H-βNal-His-AHCP-aminomethyl)-benzimidazole
2-(H-Nbg-His-AHCP-aminomethyl)-benzimidazole
2-(H-Nle-His-AHCP-aminomethyl)-benzimidazole
2-(H-Orn-His-AHCP-aminomethyl)-benzimidazole
2-(H-Pro-His-AHCP-aminomethyl)-benzimidazole
2-(H-Ser-His-AHCP-aminomethyl)-benzimidazole
2-(H-Thr-His-AHCP-aminomethyl)-benzimidazole
2-(H-Tic-His-AHCP-aminomethyl)-benzimidazole
2-(H-Trp-His-AHCP-aminomethyl)-benzimidazole
2-(H-Tyr-His-AHCP-aminomethyl)-benzimidazole
2-(H-Val-His-AHCP-aminomethyl)-benzimidazole
2-(1S-H-Abu-His-AHCP-amino-3-methylbutyl)-benzimidazole
2-(1S-H-Ada-His-AHCP-amino-3-methylbutyl)-benzimidazole
2-(1S-H-Ala-His-AHCP-amino-3-methylbutyl)-benzimidazole
2-(1S-H-Arg-His-AHCP-amino-3-methylbutyl)-benzimidazole
2-(1S-H-Asn-His-AHCP-amino-3-methylbutyl)-benzimidazole
2-(1S-H-Bia-His-AHCP-amino-3-methylbutyl)-benzimidazole
2-(1S-H-Cal-His-AHCP-amino-3-methylbutyl)-benzimidazole
2-(1S-H-Dab-His-AHCP-amino-3-methylbutyl)-benzimidazole
2-(1S-H-Gln-His-AHCP-amino-3-methylbutyl)-benzimidazole
2-(1S-H-Gly-His-AHCP-amino-3-methylbutyl)-benzimidazole
2-(1S-H-His-AHCP-amino-3-methylbutyl)-benzimidazole
2-(1S-H-N(im)-methyl-His-His-AHCP-amino-3-methylbutyl)-benzimidazole
2-(1S-H-Ile-His-AHCP-amino-3-methylbutyl)-benzimidazole
2-(1S-H-Leu-His-AHCP-amino-3-methylbutyl)-benzimidazole
2-(1S-H-tert.-Leu-His-AHCP-amino-3-methylbutyl)-benzimidazole
2-(1S-H-Lys-His-AHCP-amino-3-methylbutyl)-benzimidazole
2-(1S-H-Met-His-AHCP-amino-3-methylbutyl)-benzimidazole
2-(1S-H-αNal-His-AHCP-amino-3-methylbutyl)-benzimidazole
2-(1S-H-βNal-His-AHCP-amino-3-methylbutyl)-benzimidazole
2-(1S-H-Nbg-His-AHCP-amino-3-methylbutyl)-benzimidazole
2-(1S-H-Nle-His-AHCP-amino-3-methylbutyl)-benzimidazole
2-(1S-H-Orn-His-AHCP-amino-3-methylbutyl)-benzimidazole
2-(1S-H-Pro-His-AHCP-amino-3-methylbutyl)-benzimidazole
2-(1S-H-Ser-His-AHCP-amino-3-methylbutyl)-benzimidazole
2-(1S-H-Thr-His-AHCP-amino-3-methylbutyl)-benzimidazole
2-(1S-H-Tic-His-AHCP-amino-3-methylbutyl)-benzimidazole 2-(1S-H-Trp-His-AHCP-amino-3-methylbutyl)-benzimidazole
2-(1S-H-Tyr-His-AHCP-amino-3-methylbutyl)-benzimidazole
2-(1S-H-Val-His-AHCP-amino-3-methylbutyl)-benzimidazole
2-(H-Abu-His-AHCP-Ile-aminomethyl)-benzimidazole
2-(H-Ada-His-AHCP-Ile-aminomethyl)-benzimidazole
2-(H-Ala-His-AHCP-Ile-aminomethyl)-benzimidazole
2-(H-Arg-His-AHCP-Ile-aminomethyl)-benzimidazole
2-(H-Asn-His-AHCP-Ile-aminomethyl)-benzimidazole
2-(H-Bia-His-AHCP-Ile-aminomethyl)-benzimidazole
2-(H-Cal-His-AHCP-Ile-aminomethyl)-benzimidazole
2-(H-Dab-His-AHCP-Ile-aminomethyl)-benzimidazole
2-(H-Gln-His-AHCP-Ile-aminomethyl)-benzimidazole
2-(H-Gly-His-AHCP-Ile-aminomethyl)-benzimidazole
2-(H-His-His-AHCP-Ile-aminomethyl)-benzimidazole
2-(H-N(im)-methyl-His-His-AHCP-Ile-aminomethyl)-benzimidazole
2-(H-Ile-His-AHCP-Ile-aminomethyl)-benzimidazole
2-(H-Leu-His-AHCP-Ile-aminomethyl)-benzimidazole
2-(H-tert.-Leu-His-AHCP-Ile-aminomethyl)-benzimidazole
2-(H-Lys-His-AHCP-Ile-aminomethyl)-benzimidazole
2-(H-Met-His-AHCP-Ile-aminomethyl)-benzimidazole
2-(H-αNal-His-AHCP-Ile-aminomethyl)-benzimidazole
2-(H-βNal-His-AHCP-Ile-aminomethyl)-benzimidazole
2-(H-Nbg-His-AHCP-Ile-aminomethyl)-benzimidazole
2-(H-Nle-His-AHCP-Ile-aminomethyl)-benzimidazole
2-(H-Orn-His-AHCP-Ile-aminomethyl)-benzimidazole
2-(H-Pro-His-AHCP-Ile-aminomethyl)-benzimidazole
2-(H-Ser-His-AHCP-Ile-aminomethyl)-benzimidazole
2-(H-Thr-His-AHCP-Ile-aminomethyl)-benzimidazole
2-(H-Tic-His-AHCP-Ile-aminomethyl)-benzimidazole
2-(H-Trp-His-AHCP-Ile-aminomethyl)-benzimidazole
2-(H-Tyr-His-AHCP-Ile-aminomethyl)-benzimidazole
2-(H-Val-His-AHCP-Ile-aminomethyl)-benzimidazole
2-(1S-H-Abu-His-AHCP-Ile-amino-3-methylbutyl)-benzimidazole
2-(1S-H-Ada-His-AHCP-Ile-amino-3-methylbutyl)-benzimidazole
2-(1S-H-Ala-His-AHCP-Ile-amino-3-methylbutyl)-benzimidazole
2-(1S-H-Arg-His-AHCP-Ile-amino-3-methylbutyl)-benzimidazole
2-(1S-H-Asn-His-AHCP-Ile-amino-3-methylbutyl)-benzimidazole
2-(1S-H-Bia-His-AHCP-Ile-amino-3-methylbutyl)-benzimidazole
2-(1S-H-Cal-His-AHCP-Ile-amino-3-methylbutyl)-benzimidazole
2-(1S-H-Dab-His-AHCP-Ile-amino-3-methylbutyl)-benzimidazole
2-(1S-H-Gln-His-AHCP-Ile-amino-3-methylbutyl)-benzimidazole
2-(1S-H-Gly-His-AHCP-Ile-amino-3-methylbutyl)-benzimidazole
2-(1S-H-His-His-AHCP-Ile-amino-3-methylbutyl)-benzimidazole
2-(1S-H-N(im)-methyl-His-His-AHCP-Ile-amino-3-methylbutyl)-benzimidazole
2-(1S-H-Ile-His-AHCP-Ile-amino-3-methylbutyl)-benzimidazole
2-(1S-H-Leu-His-AHCP-Ile-amino-3-methylbutyl)-benzimidazole
2-(1S-H-tert.-Leu-His-AHCP-Ile-amino-3-methylbutyl)-benzimidazole
2-(1S-H-Lys-His-AHCP-Ile-amino-3-methylbutyl)-benzimidazole
2-(1S-H-Met-His-AHCP-Ile-amino-3-methylbutyl)-benzimidazole
2-(1S-H-αNal-His-AHCP-Ile-amino-3-methylbutyl)-benzimidazole
2-(1S-H-βNal-His-AHCP-Ile-amino-3-methylbutyl)-benzimidazole
2-(1S-H-Nbg-His-AHCP-Ile-amino-3-methylbutyl)-benzimidazole
2-(1S-H-Nle-His-AHCP-Ile-amino-3-methylbutyl)-benzimidazole
2-(1S-H-Orn-His-AHCP-Ile-amino-3-methylbutyl)-benzimidazole
2-(1S-H-Pro-His-AHCP-Ile-amino-3-methylbutyl)-benzimidazole
2-(1S-H-Ser-His-AHCP-Ile-amino-3-methylbutyl)-benzimidazole
2-(1S-H-Thr-His-AHCP-Ile-amino-3-methylbutyl)-benzimidazole
2-(1S-H-Tic-His-AHCP-Ile-amino-3-methylbutyl)-benzimidazole
2-(1S-H-Trp-His-AHCP-Ile-amino-3-methylbutyl)-benzimidazole
2-(1S-H-Tyr-His-AHCP-Ile-amino-3-methylbutyl)-benzimidazole
2-(1S-H-Val-His-AHCP-Ile-amino-3-methylbutyl)-benzimidazole
2(H-Phe-His-AHCP-Abu-aminomethyl)-benzimidazole
2(H-Phe-His-AHCP-Ala-aminomethyl)-benzimidazole
2(H-Phe-His-AHCP-Cal-aminomethyl)-benzimidazole
2(H-Phe-His-AHCP-Gly-aminomethyl)-benzimidazole
2(H-Phe-His-AHCP-Leu-aminomethyl)-benzimidazole
2(H-Phe-His-AHCP-Leu-aminomethyl)-1H-imidazo[4,5-b]pyridine
2(H-Phe-His-AHCP-Leu-aminomethyl)-1H-imidazo[4,5-c]pyridine
2(H-Phe-His-AHCP-Met-aminomethyl)-benzimidazole
2(H-Phe-His-AHCP-Nle-aminomethyl)-benzimidazole
2(H-Phe-His-AHCP-Val-aminomethyl)-benzimidazole
2-(1S-H-Phe-His-AHCP-Abu-amino-3-methylbutyl)-benzimidazole
2-(1S-H-Phe-His-AHCP-Ala-amino-3-methylbutyl)-benzimidazole
2-(1S-H-Phe-His-AHCP-Cal-amino-3-methylbutyl)-benzimidazole
2-(1S-H-Phe-His-AHCP-Gly-amino-3-methylbutyl)-benzimidazole
2-(1S-H-Phe-His-AHCP-Leu-amino-3-methylbutyl)-benzimidazole
2-(1S-H-Phe-His-AHCP-Leu-amino-3-methylbutyl)-1H-imidazo[4,5-b]pyridine
2-(1S-H-Phe-His-AHCP-Leu-amino-3-methylbutyl)-1H-imidazo[4,5-c]pyridine
2-(1S-H-Phe-His-AHCP-Met-amino-3-methylbutyl)-benzimidazole
2-(1S-H-Phe-His-AHCP-Nle-amino-3-methylbutyl)-benzimidazole
2-(1S-H-Phe-His-AHCP-Val-amino-3-methylbutyl)-benzimidazole
2-(H-Phe-His-AHCP-aminomethyl)-benzimidazole
2-(H-Phe-His-AHCP-aminomethyl-1H-imidazo[4,5-b]pyridine
2-(H-Phe-His-AHCP-aminomethyl-1H-imidazo[4,5-c]pyridine
2-(1S-H-Phe-His-AHCP-aminoethyl)-benzimidazole
2-(1S-H-Phe-His-AHCP-aminopropyl)-benzimidazole
2-(1S-H-Phe-His-AHCP-aminobutyl)-benzimidazole 2-(1S-H-Phe-His-AHCP-amino-2-methylbutyl)-benzimidazole
2-(1S-H-Phe-His-AHCP-amino-3-methylbutyl)-1H-imidazo[4,5-b]pyridine
2-(1S-H-Phe-His-AHCP-amino-3-methylbutyl)-1H-imidazo[4,5-c]pyridine
2-(1S-H-Phe-His-AHCP-amino-3-methylbutyl)-benzoxazole
2-(1S-H-Phe-His-AHCP-amino-3-methylbutyl)-benzthiazole
2-(H-Phe-His-AHCP-Ile-aminomethyl)-benzimidazole
2-(H-Phe-His-AHCP-Ile-aminomethyl)-1H-imidazo[4,5-b]pyridine
2-(H-Phe-His-AHCP-Ile-aminomethyl)-1H-imidzao[4,5-c]pyridine
2-(1S-H-Phe-His-AHCP-Ile-aminoethyl)-benzimidazole
2-(1S-H-Phe-His-AHCP-Ile-aminopropyl)-benzimidazole
2-(1S-H-Phe-His-AHCP-Ile-aminobutyl)-benzimidazole
2-(1S-H-Phe-His-AHCP-Ile-amino-2-methylbutyl)-benzimidazole
2-(1S-H-Phe-His-AHCP-Ile-amino-3-methylbutyl)-1H-imidazo[4,5-b]pyridine
2-(1S-H-Phe-His-AHCP-Ile-amino-3-methylbutyl)-1H-imidazo[4,5-c]pyridine
2-(1S-H-Phe-His-AHCP-Ile-amino-3-methylbutyl)-benzoxazole
2-(1S-H-Phe-His-AHCP-Ile-amino-3-methylbutyl)-benzthiazole.

Example 10

1 g of 2-(1-CBZ-Phe-His-AHCP-aminomethyl)benzimidazole is dissolved in 10 ml of ethanol, hydrogenated on 0.5 g of 10% Pd-C at 20° and under 1 bar for 3 h, and the mixture is filtered, the filtrate evaporated and, after purification by chromatography, 2-(1-H-Phe-His-AHCP-aminomethyl)benzimidazole is obtained.

The following are obtained analogously:
2-(1S-BOC-Phe-Dab-AHCP-Ile-amino-3-methylbutyl)-benzimidazole from 2-[1S-BOC-Phe-(4-CBZ-Dab)-AHCP-Ile-amino-3-methylbutyl]benzimidazole;
2-(1S-BOC-Phe-Orn-AHCP-Ile-amino-3-methylbutyl)-benzimidazole from 2-[1S-BOC-Phe-(5-CBZ-Orn)-AHCP-Ile-amino-3-methylbutyl]benzimidazole;
2-(1S-BOC-Phe-Lys-AHCP-Ile-amino-3-methylbutyl)-benzimidazole from 2-[1S-BOC-Phe-(6-CBZ-Lys)-AHCP-Ile-amino-3-methylbutyl]benzimidazole.

The examples which follow relate to pharmaceutical formulations.

Example A: Injection vials

A solution of 100 g of 2-(BOC-Phe-His-AHCP-aminomethyl)benzimidazole formate and 5 g of disodium hydrogen phosphate in 3 l of double-distilled water is adjusted to pH 6.5 with 2N hydrochloric acid, is filtered sterile, dispensed into injection vials, freeze-dried under sterile conditions and closed sterile. Each injection vial contains 500 mg of active compound.

Example B: Suppositories

A mixture of 500 g of 2-(1S-BOC-Phe-His-AHCP-Ile-amino-3-methylbutyl)benzimidazole with 100 g of soya lecithin and 1,400 g of cocoa butter is melted, poured into moulds and allowed to cool. Each suppository contains 500 mg of active compound.

The preceding examples can be repeated with similar success by substituting the generic of specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An amino acid derivative of the formula $$X-Z-NR^2-CHR^3-CHR^4-(CHR^5)_n-CO-$$
$$B-D$$

in which

X is H, $R^1-O-C_mH_{2m}-CO-$, $R^1-C_mH_{2m}-O-CO-$, $R^1-C_mH_{2m}-CO-$, $R1-SO_2-$, $(R^1-C_mH_{2m})-L(R^1-C_pH_{2p}-$ $C_rH_{2r}-CO-$, $H-(NHCH_2CH_2)_m-NH-CH_2CO-$ or 9-fluorenyl-$C_mH_{2m}-O-CO-$, Z is 0 to 4 amino acid residues which are bonded together in the manner of a peptide, each being Abu, Ada, Ala, Arg, Asn, Bia, Cal, Dab, Gln, Gly, His, N(im)-alkyl-His, Ile, Leu, tert.-Leu, Lys, Met, αNal, βNal, Nbg, Nle, Orn, Phe, Pro, Ser, Thr, Tic, Trp, Tyr or Val, B is absent or is Abu, Ala, Cal, Gly, Ile, Leu, Met, Nle or Val, D is

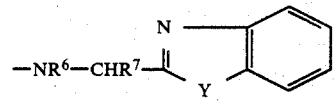

or the latter in which one or more CH groups in the benzene ring are replaced by N, Y is NH, O or S, $R^1$ and $R^3$ are each independently A; Ar; Ar-alkyl; A, Ar, or Ar-alkyl each substituted by A, AO, Hal, or a combination thereof; cycloalkyl with 3–7C atoms; cycloalkyl-alkyl with 4–11C atoms; bicycloalkyl or tricycloalkyl, each of 7–14C atoms; or bicycloalkylalkyl or tricycloalkylalkyl, each of 8–18C atoms, $R^2$, $R^5$ and $R^6$ are each independently H or A, $R^4$ is OH or $NH_2$, $R^7$ is H, A, cycloalkylalkyl or Ar-alkyl, L is CH or N, m, p and r are each independently 0, 1, 2, 3, 4 or 5, n is 1 or 2, Ar is naphthyl, phenyl, or phenyl substituted by A, AO, Hal, $CF^3$, OH, $NH^2$, or a combination thereof, Hal is F, Cl, Br or I, and A is alkyl of 1–8C atoms, wherein A, Ar, Hal and alkyl are each chosen independently, and wherein one or more —NH—CO groups are replaced by —NA—CO— groups, or a pharmacologically acceptable salt thereof.

2. A compound of claim 1, wherein

X is H, BOC, POA, CBZ, 2-phenylbutyryl, 2-benzyl-3-phenylpropionyl, 2-benzyl-4-phenylbutyryl, 2-(2- phenylethyl-4-phenylbutyryl) or 2-(2-naphthylmethyl)-4-phenylbutyryl,

Z is absent or is His, Ada-His, Cal-His, αNal-His, βNal-His, Phe-Abu, Phe-Bia, Phe-DAB, Phe-His, Phe-N-(im)-methyl-His, Phe-Leu, Phe-Lys, Phe-Met, Phe-Nle or Phe-Orn, $R^2$ and $R^5$ are H, $R^3$ is isobutyl, cyclohexylmethyl, 2-cyclohexylethyl or benzyl, n is 1, B is absent or is Ile or Leu, D is —NH—CHR$^7$-(benzimidazol-2-yl) and $R^7$ is H or alkyl which has 1–4C atoms.

3. A compound of claim 1,
wherein
X is H, BOC, 2-benzyl-3-phenylpropionyl, 2-benzyl-4-phenylbutyryl or 2-(2-phenylethyl)-4-phenylbutyryl, Z is His, Ada-His, Cal-His, α-Nal-His, β-Nal-His, Phe-Abu, Phe-Bia, Phe-Dab, Phe-His, Phe-N(im)-methyl-His, Phe-Leu, Phe-Lys, Phe-Met, Phe-Nle or Phe-Orn, $R^2$ and $R^5$ are H, $R^3$ is cyclohexylmethyl, $R^4$ is OH, n is 1, B is absent or Ile, D is —NH—CHR$^7$-(benzimidazol-2-yl) and $R^7$ is H or alkyl which has 1–4C atoms.

4. A compound of claim 1,
wherein
X is BOC or 2-benzyl-4-phenylbutyryl,
Z is His or Phe-His,
$R^2$ and $R^5$ are each H,
$R^3$ is cyclohexylmethyl,
$R^4$ is OH,
n is 1,
B is absent or Ile,
D is —NH—CHR$^7$-(benzimidazol(2-yl) and
$R^7$ is H or isobutyl.

5. A compound of claim 1 wherein Z is 2 amino acid residues.

6. A compound of claim 1 wherein Z is His, Phe-His, Pro-Phe-His or His-Pro-Phe-His, as well as preferably the groups Abu, Ada, Asn, Bia, Cal, Gln, N-(im)-methyl-His, Leu, αNal, βNal, Nle, Phe, Trp, Tyr, Abu-His, Ada-His, Ala-His, Ala-Phe, Arg-His, Asn-His, Bia-His, Cal-His, Dab-His, Gly-His, His-His, Ile-His, Leu-His, tert.-Leu-His, Lys-His, Met-His, αNal-His, βNal-His, Nbg-His, Nle-His, (N-Me-His)-His, (N-Me-Phe)-His, Orn-His, Phe-Abu, Phe-Ada, Phe-Ala, Phe-Arg, Phe-Asn, Phe-Bia, Phe-Cal, Phe-Dab, Phe-Gln, Phe-Gly, Phe-(N-im-methyl-His), Phe-Ile, Phe-Leu, Phe-tert.-Leu, Phe-Lys, Phe-Met, Pheα-Nal, Phe-β-Nal, Phe-Nbg, Phe-Nle, Phe-(N-Me-His), Phe-(N-Me-Phe), Phe-Orn, Phe-Phe, Phe-Pro, Phe-Ser, Phe-Thr, Phe-Tic, Phe-Trp, Phe-Tyr, Phe-Val, Pro-His, Ser-His, Thr-His, Tic-His, Trp-His, Tyr-His, Val-His, as well as Ada-Phe-His, Pro-Ala-His, Pro-Ala-Phe, Pro-Phe-Ala, Pro-Phe-Phe, His-Pro-Ala-His, His-Pro-Ala-Phe, His-Pro-Phe-Phe, as well as Pro-Abu-His, Pro-Ada-His, Pro-Arg-His, Pro-Asn-His, Pro-Bia-His, Pro-Dab-His, Pro-Gly-His, Pro-His-His, Pro-Ile-His, Pro-Leu-His, Pro-tert.-Leu-His, Pro-Lys-His, Pro-Met-His, Pro-Nbg-His, Pro-Nle-His, Pro-(N-Me-His)-His, Pro-(N-Me-Phe)-His, Pro-Orn-His, Pro-Phe-Abu, Pro-Phe-Ada, Pro-Phe-Arg, Pro-Phe-Asn, Pro-Phe-Bia, Pro-Phe-Dab, Pro-Phe-Gln, Pro-Phe-Gly, Pro-Phe-(N-im-methyl-His), Pro-Phe-Ile, Pro-Phe-Leu, Pro-Phe-tert.-Leu, Pro-Phe-Lys, Pro-Phe-Met, Pro-Phe-Nbg, Pro-Phe-Nle, Pro-Phe-(N-Me-His), Pro-Phe-(N-Me-Phe), Pro-Phe-Onr, Pro-Phe-Pro, Pro-Phe-Ser, Pro-Phe-Thr, Pro-Phe-Tic, Pro-Phe-Trp, Pro-Phe-Tyr, PrO-Phe-Val, Pro-Pro-His, Pro-Ser-His, Pro-Thr-His, Pro-Tic-His, Pro-Trp-His, Pro-Tyr-His, Pro-Val-His, His-Pro-Abu-His, His-Pro-Ada-His, His-Pro-Arg-His, His-Pro-Asn-His, His-Pro-Bia-His, His-Pro-Dab-His, His-Pro-Gly-His, His-Pro-His-His, His-Pro-Ile-His, His-Pro-Leu-His, His-Pro-tert.-Leu-His, His-Pro-Lys-His, His-Pro-Met-His, His-Pro-Nbg-His, His-Pro-Nle-His, His-Pro-(N-Me-His)-His, His-Pro-(N-Me-Phe)-His, His-Pro-Orn-His, His-Pro-Phe-Abu, His-Pro-Phe-Ada, His-Pro-Phe-Arg, His-Pro-Phe-Asn, His-Pro-Phe-Bia, Bis-Pro-Phe-Dab, His-Pro-Phe-Gln, His-Pro-Phe-Gly, His-Pro-Phe(N-im-methyl-His), His-Pro-Phe-Ile, His-Pro-Phe-Leu, His-Pro-Phe-Phe-tert.-Leu, His-Pro-Phe-Lys, His-Pro-Phe-Met, His-Pro-Phe-Nbg, His-Pro-Phe-Nle, His-Pro-Phe-(N-Me-His), His-Pro-Phe-(N-Me-Phe), His-Pro-Phe-Orn, His-Pro-Phe-Pro, His-Pro-Phe-Ser, His-Pro-Phe-Thr, His-Pro-Phe-Tic, His-Pro-Phe-Trp, His-Pro-Phe-Tyr, His-Pro-Phe-Val, His-Pro-Pro-His, His-Pro-Ser-His, His-Pro-Thr-His, His-Pro-Tic-His, His-Pro-Trp-His, His-Pro-Tyr-His, or His-Pro-Val-His.

7. A compound of claim 1, wherein the heterocyclic ring in D is benzimidazol-2-yl.

8. A compound of claim 1, wherein W is AHCP, AHCH, Sta or AHPP.

9. A compound of claim 1, wherein W is —NH—CHR$^3$—CHOH—CH$_2$—CO—.

10.
(a) 2-(1S-BOC-Phe-His-AHCP-amino-3-methyl-butyl)-benzimidazole;
(b) 2-[1S-(2-benzyl-4-phenylbutyryl-His-AHCP-amino)-3-methyl-butyl]-benzimidazole; or
(c) 2-(1S-BOC-Phe-His-AHCP-Ile-amino-3-methyl-butyl)-benzimidazole, each of a compound of claim 1.

11. A pharmaceutical formulation comprising a compound of claim 1 and a pharmaceutically acceptable carrier.

12. A pharmaceutical composition comprising 5–500 mg. of a compound of claim 1 and a pharmaceutically acceptable carrier.

13. A method of treating renin-dependent hypertension comprising administering a compound of claim 1.

14. A method of treating hyperaldosteronism comprising adminstering a compound of claim 1.

15. A method of treating cardiac insufficiency comprising administering a compound of claim 1.

16. A method for prophylaxis of hypertension, cardiac insufficiency or hyperaldosteronism comprising administering a compound of claim 1.

17. A method of claim 13, wherein said compound is 2-(BOC-PHE-HIS-AHCP-LEU-AMINOMETHYL)-1H-IMIDAZO(4,5-C)-PYRIDINE.

* * * * *